(12) United States Patent
Chi

(10) Patent No.: US 7,863,488 B2
(45) Date of Patent: Jan. 4, 2011

(54) SYNTHESIS OF ACENES AND HYDROXY-ACENES

(75) Inventor: Xiaoliu Chi, Kingsville, TX (US)

(73) Assignees: Alcatel-Lucent USA Inc., Murray Hill, NJ (US); Columbia University, New York, NY (US)

( * ) Notice: Subject to any disclaimer, the term of this patent is extended or adjusted under 35 U.S.C. 154(b) by 0 days.

(21) Appl. No.: 12/701,937

(22) Filed: Feb. 8, 2010

(65) Prior Publication Data

US 2010/0144086 A1 Jun. 10, 2010

Related U.S. Application Data

(62) Division of application No. 11/323,799, filed on Dec. 30, 2005, now abandoned.

(51) Int. Cl.
*C07C 35/44* (2006.01)
*C07C 5/367* (2006.01)
*H01L 51/00* (2006.01)

(52) U.S. Cl. .......................... 568/808; 585/360; 257/40

(58) Field of Classification Search ....................... None
See application file for complete search history.

(56) References Cited

U.S. PATENT DOCUMENTS 6,974,877 B2   12/2005   Vogel et al.

2003/0100779 A1   5/2003   Vogel et al.
2005/0258417 A1   11/2005   Minakata
2007/0154624 A1   7/2007   Chi

OTHER PUBLICATIONS

Dorwald, F.A.; "Side Reactions in Organic Synthesis"; Wiley-VCH: Weinheim, 2004; IX and 1-16.
Harvey, R.G.; "Polycyclic Aromatic Hydrocarbons"; Cambridge University Press: NY, 1991); 100-101, 373-376.
Fueno, T., et al.; Journal Physical Chemistry, 63, 1940 (1959).
Brzezinski, Bogumil, et al.; Journal of Physical Chemistry; 98, 2271 (1994).
Murthy, Parameshwara; University Chemistry, vol. 11 (New Age International, 1996), p. 303.
Ershov, V.V., et al.; "Tautomeric Transformations of Phenols"; Russian Chemical Reviews, (1996); 817-833.
Anthony, John E., et al.; "A Road Map to Stable, Soluble, Easily Crystallized Pentacene Derivatives"; American Chemical Society, Sep. 10, 2001, pp. A-D.
Bruckner, V., et al.; Einfache Synthese Des Pentacens; Tetrahedron Letters No. 1, 1960, pp. 5-6, Pergamon Press Ltd., printed in Great Britain.
Sparfel, D., et al.; "Transformations Thermiques Des Photooxydes Meso Des Acenes -VI", 1980 Tetrahedron vol. 36, No. 15-E, pp. 2225 to 2235.

*Primary Examiner*—Brian J Davis
(74) *Attorney, Agent, or Firm*—Hitt Gaines, PC

(57) ABSTRACT

A method comprising reducing an acenequinone to form an acenepolyhydrodiol by exposing the acenequinone to a reducing environment comprising an alkoxyaluminate.

19 Claims, 2 Drawing Sheets

SYNTHESIS OF ACENES AND HYDROXY-ACENES

CROSS-REFERENCE TO RELATED APPLICATIONS

This Application is a Divisional of U.S. application Ser. No. 11/323,799 filed on Dec. 30, 2005 now abandoned, to Xiaoliu Chi, entitled, "SYNTHESIS OF ACENES AND HYDROXY-ACENES", commonly assigned with the present invention, and, incorporated herein by reference in its entirety.

This invention was made with U.S. government support from Department of Energy grant DEFG02-04ER46118. The U.S. government has certain rights to this invention.

TECHNICAL FIELD OF THE INVENTION

The present invention is directed, in general, to the synthesis of organic molecules used in electrical devices, compositions comprising such molecules and the manufacture of electronic devices using such molecules.

BACKGROUND OF THE INVENTION

There is great interest in the use of aromatic organic molecules, such as acenes, to form semiconductive films in electronic devices as an alternative to conventional inorganic semiconductors, such as silicon. As well known to those of ordinary skill in the art, acenes are polycyclic aromatic hydrocarbons consisting of fused benzene rings in a rectilinear arrangement. For instance, the use of aromatic organic molecules like pentacene instead of silicon would eliminate the costs of silicon processing in the fabrication of thin film field effect transistor (FET) devices. The use of semiconductive films made of aromatic organic molecules could provide other advantages, such as a reduced number of steps for device fabrication, or the ability to produce flexible electronic devices.

Unfortunately, certain conventional synthetic routes for some aromatic organic molecules are undesirable. For example, the conventional synthesis of pentacene as described by Bruckner et al., Tetrahedron Letters (1960) 1:5-6, involves the use of carbon tetrachloride and mercuric chloride. Carbon tetrachloride and mercuric chloride are identified as being toxic. See e.g., *Fifth Annual Report on Carcinogens*, Substances "Known to be Carcinogenic," National Toxicology Program, Report NTP 89-239, 1989.

Additionally, pentacene and other acenes have low solubility in organic solvents. This, in turn, deters the use of low-cost solution deposition processes to deposit thin semiconductive films of such molecule in the formation of electronic devices.

SUMMARY OF THE INVENTION

To address one or more of the above-discussed deficiencies, one embodiment is a method. The method comprises reducing an acenequinone to form an acenepolyhydrodiol therefrom by exposing the acenequinone to a reducing environment comprising an alkoxyaluminate.

Another embodiment is a composition comprising an asymmetrically hydroxy-substituted acene, wherein at most one hydroxyl group is covalently bound per individual benzene ring of the acene.

A third embodiment is a manufacturing an electrical device that comprises providing a substrate and forming a matrix comprising an acenepolyhydrodiol over the substrate.

BRIEF DESCRIPTION OF THE DRAWINGS

Various embodiments are understood from the following detailed description, when read with the accompanying figures. Various features may not be drawn to scale and may be arbitrarily increased or reduced in size for clarity of discussion. Reference is now made to the following descriptions taken in conjunction with the accompanying drawings, in which.

DETAILED DESCRIPTION

The present invention recognizes the benefits of synthesizing acenes via two consecutive reduction reactions. In the first reduction reaction, an acenequinone of the target acene is converted into an acenepolyhydrodiol. In the second reduction reaction, the acenepolyhydrodiol can be converted to the target acene. Alternatively, the acenepolyhydrodiol can be thermally converted into a hydroxy-substituted acene. These reactions advantageously reduce the need for toxic compounds for the synthesis. In addition, some of the acenepolyhydrodiols or hydroxy-substituted acenes are soluble in organic solvents, thereby facilitating the fabrication of devices via solution deposition processes.

Figure 1:
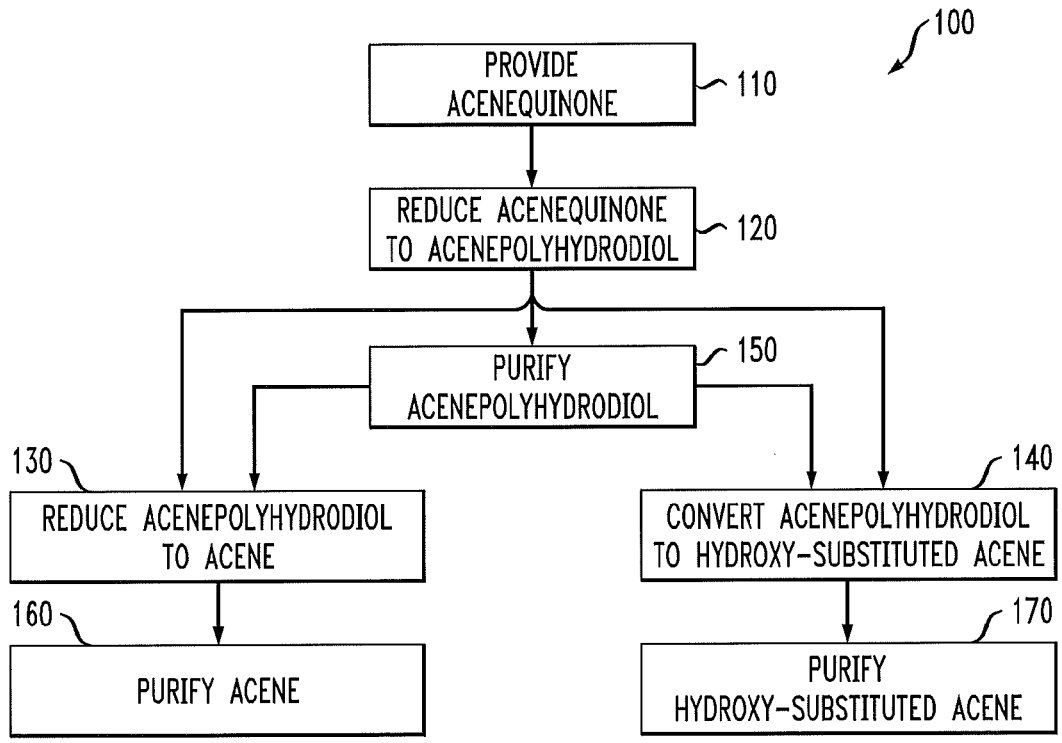
FIG. 1 presents a flow diagram showing selected steps in an exemplary method of synthesis.

One embodiment is a method of synthesis. FIG. 1 presents a flow diagram showing selected steps in an exemplary method of synthesis. In step 110, an acenequinone of the target acene is provided. In step 120, the acenequinone is reduced to form an acenepolyhydrodiol by exposing the acenequinone to a first reducing environment that includes an alkoxyaluminate. The term acenepolyhydrodiol as used herein refers to an acene derivative with two hydroxy groups added to each one or more of its benzene rings (benzo-ring groups), thereby forming a cyclohexenediol. Examples of alkoxyaluminate reducing agents include lithium alkoxyaluminum hydrides such as lithium tri-methoxyaluminum hydride, or lithium diethoxyaluminum hydride, and more preferably, lithium tri-tert-butoxyaluminohydride LiAl(O—C—(CH$_3$)$_3$)$_3$H.

The acenepolyhydrodiol can serve as an intermediate for further reactions. In optional step 130, the acenepolyhydrodiol can be further reduced to the target acene by exposing the acenepolyhydrodiol to a second reducing environment. The number of benzo-ring groups in the target acene is the same as in the acenepolyhydrodiol. Alternatively, in optional step 140, a para-substituted acenepolyhydrodiol can be converted into an asymmetrically hydroxy-substituted acene by heating the acenepolyhydrodiol in an inert atmosphere.

The reducing agent selected to promote the reduction of acenequinones to acenepolyhydrodiols in step 120 has not previously been recognized as an important variable affecting the result of the reaction. In particular, the selection of the alkoxyaluminate as the reducing agent used in step 120 provides several critical advantages over other types of reducing agents.

An alkoxyaluminate reducing agent is less reactive than reducing agents such an inorganic aluminum hydrides like lithium aluminum hydride (LiAlH$_4$). In particular, alkoxyaluminates are less reactive to moisture in the atmosphere than inorganic aluminum hydrides. This, in turn, allows step 120 to be carried out under less stringent reaction conditions than if an inorganic aluminum hydride or similarly reactive reducing agent were used. For instance, the use of alkoxyaluminate reducing agent gives one the option of performing step 120 under ambient conditions. The term ambient conditions, as used herein refers to air at room temperature (e.g., about 20° C.), at about 1 atmosphere of pressure (e.g., about 101 kilopascals) and atmospheric humidity (e.g., the range of water content normally found in the earth's atmosphere at the surface of the earth).

On the other hand, an alkoxyaluminate, such as lithium tri-tert-butoxyaluminohydride, is more reactive than boron hydride reducing agents like $NaBH_4$ or $KBH_4$. Consequently, the use of alkoxyaluminate in step 120 allows the reaction to be completed in less than about 3 hours instead of more than seven hours, as expected when using boron hydride reducing agents like $NaBH_4$ or $KBH_4$. In addition, alkoxyaluminates are thought to be less prone to generate undesired reaction byproducts as compared to boron hydrides like $KBH_4$. Moreover, because the reaction proceeds quickly and efficiently, it is not necessary to continually add new amounts reducing agent to continue the reaction, as may be the case when using boron hydrides.

As noted above, an acenequinone of the target acene is provided as the starting material in step 110. The term acenequinone as used herein refers to a molecule having at least three fused benzo-ring groups and having two ketone functional group covalently bonded to the non-fusion ring carbons of one or more of the benzo-ring groups of the acene.

Consider as an example, pentacenequinone. As illustrated in formula (I), the non-fusion carbon atoms of the pentacene rings are numbered 1 to 14, while the fusion carbon atoms are numbered 4a to 7a and 11a to 14a:

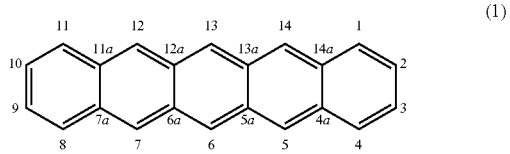

(1)

The numbering used to describe the ring carbon of the molecule shown in formula (I) and used elsewhere herein is in accordance with the International Union of Pure and Applied Chemistry's recommendations for Peripheral Numbering (Fused Ring and Bridged Fused Ring Nomenclature, Recommendation FR-5.3, Commission on Nomenclature of Organic Chemistry, 1998), which is incorporated by reference herein in its entirety.

Continuing with the example of pentacenequinone, an even number of ketone functional groups can be covalently bonded to any two of the non-fusion carbon atoms 1 to 14 forming a para-pentacenequinone. That is, two ketone functional groups are covalently bonded to two of the non-fusion carbon atoms of the same benzo-ring group, in a para-configuration. As an example, the pentacenequinone can be 6,13 pentacenequinone, as illustrated below:

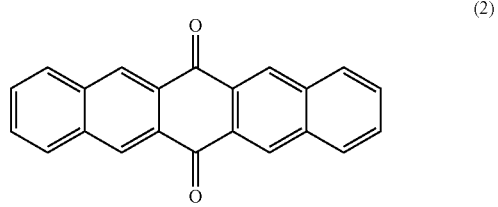

(2)

The use of acenequinones as the starting material provides several important advantages. Some acenequinones, such as 6,13 pentacenequinone, are readily available commercially, thereby eliminating the need to synthesize these molecules. Of course, in certain embodiments of the method 100, the acenequinones could be synthesized using conventional procedures well known to those of ordinary skill in the art.

Additionally, certain acenequinones, such as 6,13 pentacenequinone, are stable under ambient conditions, thereby simplifying the procedures required to handle this material. The use of acenequinones that are stable under ambient conditions is especially advantageous when the reducing agent used in the first reducing environment is also stable under ambient conditions. This is the case, for example, when the reducing agent used in step 120 comprises an alkoxyaluminate like lithium tri-tert-butoxyaluminohydride. For instance, lithium tri-tert-butoxyaluminohydride is substantially more stable in the presence of moisture (water) than other types of reducing agents, such as lithium aluminum hydride. This advantageously allows the reduction reaction in step 120 to be carried out in air, without having substantial amounts of the reducing agent react with moisture in the air.

The hydroxyl groups of the acenepolyhydrodiol are covalently bonded to the same non-fusion carbon atoms of the benzene ring that the ketone was bonded to. For instance, a para-acenequinone is reduced to a para-acenepolyhydrodiol. As an example, a para-pentacenequinone like 6,13 pentacenequinone is reduced to a para-dihydropentacenediol like 6,13 dihydropentacenediol:

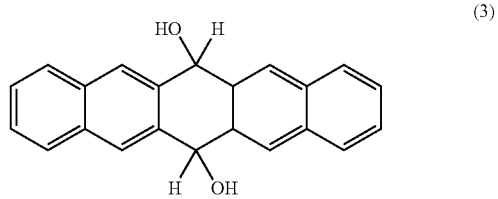

(3)

In some preferred embodiments of the method 100, step 120 includes preparing a mixture of the acenequinone and the alkoxyaluminate reducing agent in an organic solvent. Preferably, there is at least one molecule of alkoxyaluminate per ketone group in the acenequinone. For example, the mole ratio of alkoxyaluminate to acenequinone is at least about 2:1, and in some cases ranges from about 2:1 to about 3:1. The mixture is incubated for about 3 hours under ambient conditions. For example, lithium tri-tert-butoxyaluminohydride and 6,13 pentacenequinone, in a mole ratio of about 2:1 to 3:1, can be dissolved in tetrahydrofuran and then incubated for about 3 hours under ambient conditions. In some preferred cases the solution is stirred throughout the incubation. Typical yields are about 75%.

Alternatively, the reduction reaction in step 120 can be carried out in a substantially moisture-free (e.g., water free) environment. For instance, the above-described reaction can be carried out in an inert atmosphere and using solvents and reactants that have been treated to remove moisture from them. The above-described reaction using 6,13 pentacenequinone and lithium tri-tert-butoxyaluminohydride, for example, can be carried out in an argon or nitrogen atmosphere, with the use of organic solvents that have been passed through a molecular sieve to remove moisture from them.

In some cases, the reduction of the acenepolyhydrodiol to form the acene in step 130 can be done in the same reaction vessel as used in step 120, by changing the first reducing environment to the second reducing environment.

In other cases, however, before proceeding to step 130, or to step 140, it is desirable to perform an optional step 150 of purifying the acenepolyhydrodiol produced in step 120. The purification is made possible because the acenepolyhydrodiol is stable under ambient conditions. The purification step 150 can include precipitating and filtering, crystallization or chromatographic procedures.

Consider, for example, the case where 6,13 dihydropentacenediol is produced from the reaction resulting from mixing 6,13 pentacenequinone and lithium tri-tert-butoxyaluminohydride in step 120. The 6,13 dihydropentacenediol can be precipitated by acidifying the mixture, e.g., by adding dilute aqueous HCl until a light yellow precipitate is formed. The precipitated 6,13 dihydropentacenediol can then be isolated from other components of the mixture via filtration. In some cases, it is desirable to re-dissolve the precipitated 6,13 dihydropentacenediol in an organic solvent, such as hot toluene. An example of hot toluene is liquid toluene having a temperature ranging from about 80 to just below the boiling point of toluene (e.g., about 110° C.), and then re-crystallize 6,13 dihydropentacenediol. For example, the light yellow precipitate can be re-dissolved in hot toluene with white crystals of 6,13 dihydropentacenediol forming as the solution is allowed to cool to room temperature (elementary analysis: calculated, C, 84.59%, H, 5.16%; measured: C, 84.42%, H, 5.13%)

In still other cases, the 6,13 dihydropentacenediol can be purified in step 150 by passing either the product of step 120, or the above-described precipitate or re-crystallized solid via liquid chromatography. For example, the light yellow precipitate can be re-dissolved in tetrahydrofuran and then passed silica gel column using successive eluants of toluene and then tetrahydrofuran:toluene (1:9). A white cotton-like crystalline solid of the 6,13 dihydropentacenediol can be obtained by evaporating the solvents from the eluant (e.g., tetrahydrofuran and toluene).

The second reducing environment used in step 130 is different from the first environment in that the reducing agent must be capable of promoting the removal of the hydroxyl groups and donating an electron to the acene so that the molecule recovers its aromaticity. Hydride reducing agents, such as alkoxyaluminates, are unable do this. Rather, the second reducing environment comprises a reducing agent of stannous chloride. In other cases, the reducing agent can be potassium iodide (KI). In some preferred embodiments, the mole ratio of the reducing agent to acenepolyhydrodiol is about 2:1. In some embodiments, the second reducing environment is substantially free of hydrides reducing agent (e.g., less than 1 wt % alkoxyaluminate). Such may be the case, for example, when the acenepolyhydrodiol is purified in step 150 before proceeding to step 130. Of course, in other embodiments, such as when steps 120 and 130 are performed in the same reaction vessel, there can still be unreacted alkoxyaluminate present in the second reducing environment.

Analogous to step 150, the acene produced in step 130 can be purified in step 160. In some cases, for instance, the acene can be precipitated from the mixture prepared in step 130 by acidifying the mixture and isolated by filtration. Other conventional techniques such as re-crystallization or chromatography can be used to purify the acene as well.

Consider again, the example of when the acenepolyhydrodiol is 6,13 dihydropentacenediol. In some preferred embodiments, a mixture of stannous chloride and 6,13 dihydropentacenediol, in a mole ratio of 2:1, is formed by dissolving these compounds in acetone. The solution is then incubated, preferably with stirring, under ambient conditions for at least about 30 minutes, during which time a purple solid precipitates from the solution. The solid can be then isolated by centrifuging the solution, washing the solid with methanol and tetrahydrofuran, and then decanting the solvent.

The solid can be further purified in step 160 via a conventional sublimation process to give purple crystals, which are identified as pentacene by X-ray or mass spectrometry. Typical yields are about 60%. For example, the sublimation process can include heating the solid under vacuum or in argon until it evaporates, and then depositing the purple crystals on a chilled piece (e.g., on a cold finger). Non-volatile impurities can thereby be removed from the acenepolyhydrodiol. In some preferred embodiments the chilled piece comprises a temperature gradient so that the volatile impurities can also be separated by being deposited on different temperature regions.

As indicated in FIG. 1, as an alternative to step 130, a para-substituted form of the acenepolyhydrodiol can optionally be converted, in step 140, into an asymmetrically hydroxy-substituted form of the acene by heating the acenepolyhydrodiol. The term asymmetrically hydroxy-substituted acene as used herein refers to an acene having at most one hydroxyl group covalently bound per individual benzene ring of the acene. That is, there is a single hydroxyl group covalently bonded to the same carbon atom of the same benzene ring that the para-substituted diol was associated with. As an example, a para-substituted form of the acenepolyhydrodiol like 6,13 dihydropentacenediol can be converted into asymmetrically hydroxy-substituted pentacene like 6-hydroxy pentacene:

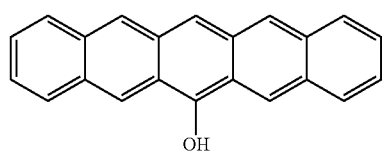

(4)

In some preferred embodiments, the heating comprises maintaining a temperature in the range from about 250 to about 300° C., for example about 280° C. for at least about 8 hours. Preferably the heating is done with the acenepolyhydrodiol in an inert atmosphere. Inert gases, such as argon or nitrogen, are preferred. For example, 6,13 dihydropentacenediol can be converted into 6-hydroxy pentacene by heating the diol at 280° C. in an inert atmosphere of argon for about 10 hours. The identity of the product can be confirmed by conventional techniques like X-ray or mass spectrometry. Typical yields are 80%.

Analogous to step 160, the asymmetrically hydroxy-substituted acene produced in step 140 can be further purified in step 170 by sublimation.

Another embodiment is a composition. The composition comprises a plurality of asymmetrically hydroxy-substituted acenes. As noted above, the asymmetrically hydroxy-substituted acene has at most one hydroxyl group covalently bound per individual benzene ring of the acene. The asymmetrically hydroxy-substituted acene can be synthesized by any of the above-described embodiments of the method discussed above in the context of FIG. 1.

In some embodiments, the plurality of asymmetrically hydroxy-substituted acenes form a semiconductive film. In some cases, the presence of one or more hydroxyl substitutions could make the solubility of the hydroxy-substituted acene in organic solvents greater than the solubility of the analogous unsubstituted acenes. This, in turn, could advantageously allow the semiconductive film to be formed using low-cost solution deposition processes, such as ink-stamping, dip-coating or spin-coating.

In other cases, the asymmetrically hydroxy-substituted acenes could be advantageously coupled to certain semiconductor substrate such as silicon. The strength of asymmetrically hydroxy-substituted acene's coupling to the silicon substrate could be stronger than the analogous acene's coupling to the substrate. For example, there may be a strong dipole-dipole interaction between the hydroxyl-group of the asymmetrically hydroxy-substituted acene and oxygen atoms covalently bonded to silicon at the substrate's surface.

In still other cases, the asymmetrically hydroxy-substituted acenes can be advantageously used as a starting material for further derivatization. For example, the hydroxyl functional group can be further modified to an ester group using techniques well known to those skilled in the art. For example the hydroxyl functional group can be converted to an ester group by reaction with acid chlorides or acid anhydrides, or by reaction with carboxylic acids in the presence of DCC (1,3-Dicyclohexylcarbodiimide) (see e.g., S. Neelakantan, R. Padmasani, and T. R. Seshadri, Tetrahedron 21:3531 (1965), incorporated by reference herein in its entirety). As another example, the hydroxyl functional group can be further modified to form an ether linkage between two of the acenes, or between the acene and an alkyl halide (see e.g., Theory of Etherification, A. W. Williamson, J. Chem. Soc., (1852), 4:106, incorporated herein in its entirety).

In certain preferred embodiments, the acene comprises from three to eight benzene rings. In some preferred embodiments, the hydroxy-substituted acene is a hydroxy-substituted pentacene. In such embodiments, the one hydroxyl group is covalently bound at one or more of the 4, 5, 6, 7 or 8 ring carbon positions of the hydroxy-substituted pentacene.

A wide variety of asymmetrically hydroxy-substituted acenes can be produced using the method discussed above in the context of FIG. 1, if the appropriate starting material, the acenequinone, is available. For example, a para-acenequinone such as 6,13 pentacenequinone can be reduced to a para-pentacenehydrodiol such as 6,13 dihydropentacenediol, which is then thermally treated to produce the hydroxy-substituted acene such as 6-hydroxy pentacene (shown in formula 4).

Alternatively, the asymmetrically hydroxy-substituted pentacene can comprise 4-hydroxy, 5-hydroxy, 6-hydroxy, 7-hydroxy, 8-hydroxy pentacene:

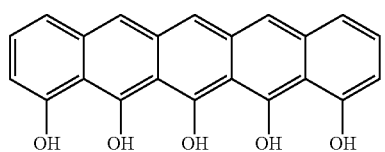

(5)

The asymmetrically hydroxy-substituted pentacene shown in formula (5) could be synthesized from a 1,4-, 5,14-, 6,13-, 7,12-, 8,11-pentacenequinone via steps 120 and then step 140. Or, the hydroxy-substituted pentacene shown in formula (5) could be synthesized from a 1,4-dihydro, 5,14-dihydro, 6,13-dihydro, 7,12-dihydro, 8,11-dihydro pentacenediol via step 140. For example, an acenequinone such as 1,4- 5,14- 6,13- 7,12-, 8,11-pentacenequinone can be reduced to an acenepolyhydrodiol such as 1,4- 5,14- 6,13- 7,12- 8,11-dihydropentacenediol, which is then thermally treated to produce the hydroxy-substituted acene such as 4,5,6,7,8-pentahydroxy pentacene.

Similarly, the asymmetrically hydroxy-substituted pentacene can comprise 4,8-dihydroxy pentacene:

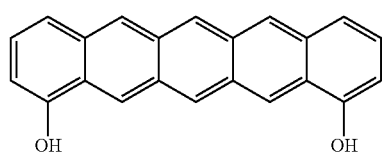

(6)

The asymmetrically hydroxy-substituted pentacene shown in formula (6) could be synthesized from a 1,4-, 8,11-pentacenequinone via steps 120 and then step 140. Or the asymmetrically hydroxy-substituted pentacene shown in formula (6) could be synthesized from a 1,4-, 8,11-dihydropentacenediol via step 140.

Figure 2:
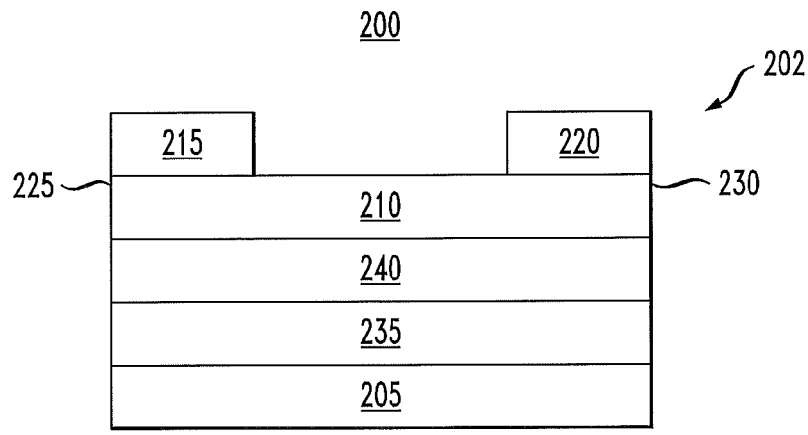
FIG. 2 presents cross-sectional view of an embodiment of an apparatus 200 that incorporates an exemplary composition.

As noted above, in some embodiments the plurality of asymmetrically hydroxy-substituted acenes forms a composition comprising a semiconductive matrix (e.g., a film or layer) in an active device. FIG. 2 presents cross-sectional view of an exemplary embodiment of an apparatus 200 that includes an active device 202 such as an organic field effect transistor (OFET).

The active device 202 can comprise a substrate 205 and an organic semiconductor matrix 210, that functions as a channel, being located over the substrate 105. The organic semiconductor matrix 210 can comprise the plurality of asymmetrically hydroxy-substituted acenes. The various components of the active device 202 can comprise any conventional material well known to those skilled in the art. For example, the substrate 205 can be made of silicon or flexible organic materials such as plastics, for example polyethylene terephthalate (PET), polyethylene napthalate (PEN), or various polyamides.

The active device 202 can further include first and second electrodes 215, 220 in contact with opposite ends 225, 230 of the organic semiconductor matrix 210. The source and drain electrodes 225, 230 can comprise e.g., gold or other electrically conductive metals or non-metals, such as electrically conductive polymers. The active device 102 can further includes a bottom gate 235 and dielectric layer 240. The bottom gate 235 can comprise doped silicon. In other cases materials more conducive to forming a flexible device, such as indium tin oxide (ITO), can be used. Similarly, the gate dielectric 240 can comprise silicon dioxide, or more flexible materials, such as polymer dielectrics like polybutyl methacrylate (PBMA).

The apparatus 200 can be used in any number of applications, such as biosensors, integrated circuits, displays, logic devices and memory devices. The active device 202 presented in FIG. 2 is a top contact bottom gate OFET device. However, one of ordinary skill in the art would understand that the active device 202 could have other conventional configurations, such as a bottom contact OFET device or top gate OFET devices, and the apparatus 200 could comprise a plurality of such devices.

Figure 3:
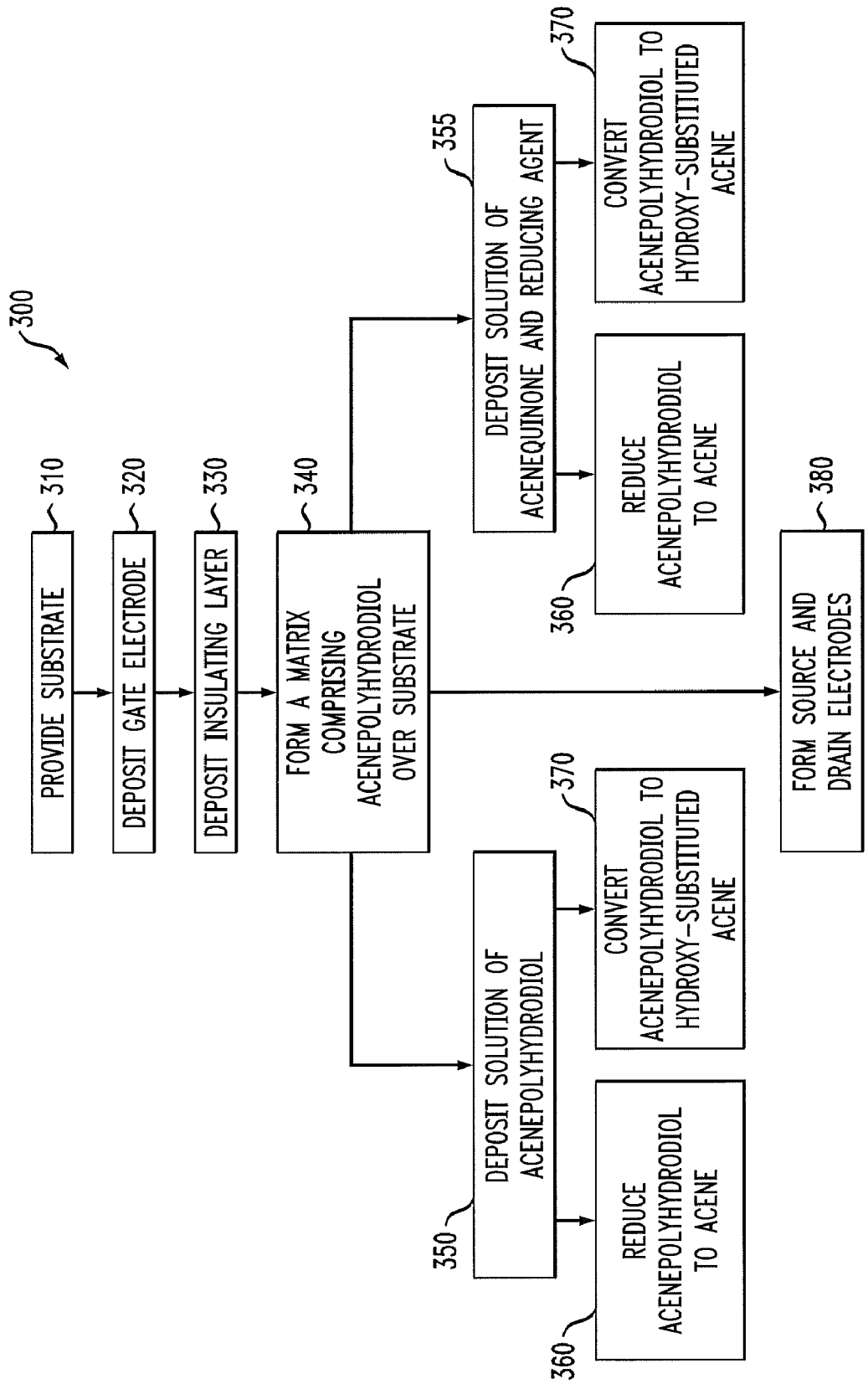
FIG. 3 presents a flow diagram showing selected steps of an exemplary method of manufacturing an active device.

Another embodiment is a method of manufacture. FIG. 3 presents a flow diagram showing selected steps of an exemplary method 300 of manufacturing an active device. Embodiments of the active device include an OFET or organic light emitting diode (OLED).

A substrate is provided in step 310. The substrate can include any conventional material. For instance, the substrate can be made of silicon or flexible organic materials such as plastics, for example, polyethylene terephthalate (PET). The substrate can also include device component layers such as a bottom gate and dielectric layer, in the case of OFET devices, or a hole injection layer and cathode in the case of OLED devices.

For example, in some embodiments of the method, the substrate comprises glass upon which are successively formed, in step 320, a gate electrode comprising physical vapor deposited indium tin oxide (ITO), and an insulating layer, in step 330, comprising spin-coated polybutyl methacrylate (PBMA). Alternatively, the substrate can comprise a silicon layer implanted with n- or p-type dopants, followed by a thermally grown $SiO_2$ dielectric layer, in steps 320 and 330, respectively.

In step 340, a matrix (e.g., a layer or film) comprising an acenepolyhydrodiol is formed over the substrate. The matrix can be used to form a thin film semiconductor in OFET devices or to form a light-emitting junction in OLED devices. The acenepolyhydrodiol can comprise any embodiments discussed above in the context of the method of synthesis and composition.

In some preferred embodiments of the method, forming the matrix comprises depositing a solution comprising the acenepolyhydrodiol over the substrate in step 350. For example, an acenepolyhydrodiol such as 6,13 dihydropentacenediol can be dissolved an organic solvent (e.g., tetrahydrofuran). This solution can then be deposited over the substrate using conventional solution deposition processes, such as ink-stamping, dip-coating or spin-coating.

In other cases, forming the matrix comprises forming a solution comprising an acenequinone and an alkoxyaluminate reducing agent (e.g., lithium tri-tert-butoxyaluminohydride), which is then deposited over the substrate in step 355. As noted above in the context of FIG. 1, an acenequinone in the appropriate reducing environment can be reduced to an acenepolyhydrodiol.

Still other embodiments of the method further comprise a step 360 of reducing the acenepolyhydrodiol to an acene by exposing the acenepolyhydrodiol to a second reducing environment. Any of the reducing environments discussed above in the context of step 130 of the method presented in FIG. 1 can be used in step 360. For example, a matrix comprising 6,13 dihydropentacenediol can be reduced to pentacene by exposing the matrix to a reducing environment comprising a reducing agent such as stannous chloride.

In alternative embodiments of the method further comprises a step 370 of converting the acenepolyhydrodiol into an asymmetrically hydroxy-substituted acene. Any of the thermal treatments discussed above in the context of step 140 of the method presented in FIG. 1 can be used in step 370. For example, it is expected that a matrix comprising 6,13 pentacenediol could be reduced to 6-hydroxyl pentacene by heating the matrix to a temperature of from 250° C. to 300° C. for about 6 to 8 hours.

In step 380, source and drain electrodes are formed on the matrix using conventional procedures. In some cases, for example, gold source and drain electrodes are deposited on the layer using a shadow mask to form an OFET device. Of course, alternative steps would be followed to deposit the anode and hole injection layers to form an OLED device. Also, further steps, well-known to those skilled in the art, could be performed to form an operative electrical device.

Although the embodiments have been described in detail, those of ordinary skill in the art should understand that they could make various changes, substitutions and alterations herein without departing from the scope of the invention.

What is claimed is:

1. A method, comprising:
reducing an acenequinone to form an acenepolyhydrodiol therefrom by exposing said acenequinone to a reducing environment comprising an alkoxyaluminum hydride.

2. The method recited in claim 1, wherein said alkoxyaluminum hydride comprises lithium tri-tert-butoxyaluminohydride.

3. The method recited in claim 1, further comprising reducing said acenepolyhydrodiol to form an acene therefrom by exposing said acenepolyhydrodiol to a second reducing environment comprising a reducing agent of stannous chloride or potassium iodide.

4. The method recited in claim 3, wherein said second reducing environment has less that 1 wt % of said alkoxyaluminum hydride.

5. The method recited in claim 3, wherein exposure to said second reducing environment includes incubating a solution containing said stannous chloride and said acenepolyhydrodiol for at least about 30 minutes.

6. The method recited in claim 3, wherein said acene is an asymmetrically hydroxy-substituted acene, wherein at most one hydroxyl group is covalently bound per individual benzene ring of said hydroxy-substituted acene.

7. The method recited in claim 3, wherein said acene comprises from three to eight benzene rings.

8. The method recited in claim 6, wherein said hydroxy-substituted acene is a hydroxy-substituted pentacene.

9. The method recited in claim 8, wherein said at most one hydroxyl group of said asymmetrically hydroxy-substituted pentacene is covalently bound at one of a 4, 5, 6, 7 or 8 non-fusion carbon ring positions.

10. The method recited in claim 1, further comprising reducing a para-substituted said acenepolyhydrodiol into an asymmetrically hydroxy-substituted acene by heating said acenepolyhydrodiol in an inert atmosphere.

11. The method of claim 10, wherein said inert atmosphere comprises argon.

12. The method recited in claim 10, wherein said heating comprises maintaining a temperature in a range from about 250 to about 300° C.

13. The method recited in claim 1, wherein said acenequinone comprises a pentacenequinone.

14. The method recited in claim 1, wherein said acenequinone comprises 6, 13 pentacenequinone.

15. The method recited in claim 1, further including manufacturing an active device, including:
providing a substrate; and
forming a semiconductive matrix on said substrate, wherein said semiconductive matrix includes said acenepolyhydrodiol formed by said reducing of said acenequinone.

16. The method of claim 15, wherein forming said semiconductive matrix comprises depositing a solution comprising said acenepolyhydrodiol on said substrate.

17. The method of claim 16, wherein forming said semiconductive matrix further comprises reducing said acenepolyhydrodiol to an acene.

18. The method of claim 16, wherein forming said semiconductive matrix further comprises heating said acenepolyhydrodiol to form an asymmetrically hydroxy-substituted.

19. The method of claim 1, wherein said alkoxyaluminum hydride is a lithium alkoxyaluminum hydride.

* * * * *